(12) United States Patent
Binette

(10) Patent No.: US 9,060,978 B2
(45) Date of Patent: Jun. 23, 2015

(54) METHOD FOR TREATING AN INTERVERTEBRAL DISC DISORDER BY ADMINISTERING A DOMINANT NEGATIVE TUMOR NECROSIS FACTOR ANTAGONIST

(75) Inventor: Francois Binette, San Francisco, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/280,073

(22) Filed: Oct. 24, 2011

(65) Prior Publication Data

US 2012/0189619 A1    Jul. 26, 2012

Related U.S. Application Data

(60) Provisional application No. 61/435,549, filed on Jan. 24, 2011.

(51) Int. Cl.
*A61K 38/19* (2006.01)
*A61K 9/00* (2006.01)
*A61K 9/50* (2006.01)

(52) U.S. Cl.
CPC ............. *A61K 38/191* (2013.01); *A61K 9/0019* (2013.01); *A61K 9/5031* (2013.01)

(58) Field of Classification Search
CPC .................................................. A61K 38/191
USPC ......................................................... 424/85.1
See application file for complete search history.

(56) References Cited

U.S. PATENT DOCUMENTS

| | | | |
|---|---|---|---|
| 4,624,255 A | 11/1986 | Schenck et al. | |
| 4,742,054 A | 5/1988 | Naftchi | |
| 4,863,457 A | 9/1989 | Lee | |
| 5,522,844 A | 6/1996 | Johnson | |
| 5,626,838 A | 5/1997 | Cavanaugh, Jr. | |
| 5,759,583 A | 6/1998 | Iwamoto et al. | |
| 5,868,789 A | 2/1999 | Huebner | |
| 5,942,241 A | 8/1999 | Chasin et al. | |
| 6,069,129 A | 5/2000 | Sandberg et al. | |
| 6,179,862 B1 | 1/2001 | Sawhney | |
| 6,248,345 B1 | 6/2001 | Goldenheim et al. | |
| 6,287,588 B1 | 9/2001 | Shih et al. | |
| 6,326,020 B1 | 12/2001 | Kohane et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,524,607 B1 | 2/2003 | Goldenheim et al. | |
| 6,534,081 B2 | 3/2003 | Goldenheim et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,723,741 B2 | 4/2004 | Jeon et al. | |
| 6,756,058 B2 | 6/2004 | Brubaker et al. | |
| 6,773,714 B2 | 8/2004 | Dunn et al. | |
| 6,921,541 B2 | 7/2005 | Chasin et al. | |
| 6,974,462 B2 | 12/2005 | Sater | |
| 7,056,695 B2 | 6/2006 | Dahiyat et al. | |
| 7,101,974 B2 | 9/2006 | Dahiyat et al. | |
| 7,144,412 B2 | 12/2006 | Wolfe et al. | |
| 7,144,987 B1 | 12/2006 | Chirino et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |
| 7,235,043 B2 | 6/2007 | Gellman et al. | |
| 7,244,823 B2 | 7/2007 | Dahiyat et al. | |
| 7,287,983 B2 | 10/2007 | Ilan | |
| 7,318,840 B2 | 1/2008 | McKay | |
| 7,329,259 B2 | 2/2008 | Cragg | |
| 7,361,168 B2 | 4/2008 | Makower et al. | |
| 7,367,978 B2 | 5/2008 | Drewry et al. | |
| 7,446,174 B2 | 11/2008 | Desjarlais et al. | |
| 7,587,286 B2 | 9/2009 | Desjarlais et al. | |
| 7,610,156 B2 | 10/2009 | Desjarlais et al. | |
| 2002/0009454 A1 | 1/2002 | Boone et al. | |
| 2002/0090398 A1 | 7/2002 | Dunn et al. | |
| 2003/0022927 A1 | 1/2003 | Jeon et al. | |
| 2003/0049256 A1 | 3/2003 | Tobinick | |
| 2003/0185826 A1 | 10/2003 | Tobinick | |
| 2003/0185873 A1 | 10/2003 | Chasin et al. | |
| 2003/0204191 A1 | 10/2003 | Sater et al. | |
| 2003/0224033 A1 | 12/2003 | Li et al. | |
| 2004/0072799 A1 | 4/2004 | Li et al. | |
| 2004/0082540 A1 | 4/2004 | Hermida Ochoa | |
| 2004/0109893 A1 | 6/2004 | Chen et al. | |
| 2004/0214793 A1 | 10/2004 | Hermida Ochoa | |
| 2005/0059744 A1 | 3/2005 | Donello et al. | |
| 2005/0142163 A1 | 6/2005 | Hunter et al. | |
| 2005/0175709 A1 | 8/2005 | Baty, III et al. | |
| 2005/0186261 A1 | 8/2005 | Avelar et al. | |
| 2005/0197293 A1 | 9/2005 | Mellis et al. | |

(Continued)

FOREIGN PATENT DOCUMENTS

| | | |
|---|---|---|
| WO | 03005961 A2 | 1/2003 |
| WO | 2005034998 A2 | 4/2005 |
| WO | 2007005177 A1 | 1/2007 |

OTHER PUBLICATIONS

Richards, Kim. "Xencor data published in Journal of Immunology demonstrate selectivity of new class of inhibitors for inflammatory disease". Jul. 23, 2007 Drugs.com; article retrieved from http://www.drugs.com/clinical_trials/xencor-data-published-journal-immunology-demonstrate-selectivity-new-class-inhibitors-inflammatory-1624.html, Feb. 19, 2013.*

(Continued)

*Primary Examiner* — Prema Mertz
(74) *Attorney, Agent, or Firm* — Sorell Lenna & Schmidt LLP

(57) ABSTRACT

Effective methods of treating a spinal disorder or osteoarthritis associated with a proinflammatory agent in a patient in need of such treatment, the method comprising administering an effective amount of DN-TNF (e.g., XPro®-1595) to a target tissue site at or near the spine or osteoarthritic joint to reduce pain and/or inflammation.

3 Claims, 5 Drawing Sheets

(56) References Cited

U.S. PATENT DOCUMENTS

| | | | |
|---|---|---|---|
| 2006/0074422 | A1 | 4/2006 | Story et al. |
| 2006/0106361 | A1 | 5/2006 | Muni et al. |
| 2006/0148903 | A1 | 7/2006 | Burch et al. |
| 2006/0183786 | A1 | 8/2006 | Wang |
| 2006/0189944 | A1 | 8/2006 | Campbell et al. |
| 2006/0228391 | A1 | 10/2006 | Seyedin et al. |
| 2007/0004790 | A1 | 1/2007 | Chow et al. |
| 2007/0156180 | A1 | 7/2007 | Jaxx et al. |
| 2007/0185497 | A1 | 8/2007 | Cauthen et al. |
| 2007/0202074 | A1 | 8/2007 | Shalaby |
| 2007/0243225 | A1 | 10/2007 | McKay |
| 2007/0243228 | A1* | 10/2007 | McKay .................. 424/426 |
| 2007/0248639 | A1 | 10/2007 | Demopulos et al. |
| 2007/0253994 | A1 | 11/2007 | Hildebrand |
| 2008/0019975 | A1* | 1/2008 | Gorman .................. 424/145.1 |
| 2008/0021074 | A1 | 1/2008 | Cartt |
| 2008/0091207 | A1 | 4/2008 | Truckai et al. |
| 2009/0020076 | A1 | 1/2009 | Ghiraldi |
| 2009/0060971 | A1 | 3/2009 | McKay |
| 2009/0062922 | A1 | 3/2009 | McKay |
| 2009/0130019 | A1 | 5/2009 | Tobinick |
| 2009/0214612 | A1 | 8/2009 | Schafer |
| 2009/0304649 | A9 | 12/2009 | McKay et al. |

OTHER PUBLICATIONS

Richards, Kim. "Xencor data published in Journal of Immunology demonstrate selectivity of new class of inhibitors for inflammatory disease". Jul. 23, 2007 Drugs.com; article retrieved from http://www.drugs.com/clinical_trials/xencor-data-published-journal-immunology-demonstrate-selectivity-new-class-inhibitors-inflammtory-1624.html, Feb. 19, 2013.*

Richards, Kim. "Xencor data published in Journal of Immunology demonstrate selectivity of new class of inhibitors for inflammatory disease". Jul. 23, 2007 Drugs.com; article retrieved from http://www.drugs.com/clinical_trials/xencor-data-published-journal-immunology-demonstrate-selectivity-new-class-inhibitors-inflammatory-1624.html. Feb. 18, 2013.*

Atrigel, Drug Delivery Platform, QLT USA, Inc., Revised Jul. 2006, 2 pages.

Elizabeth A. Moberg-Wolff, MD, Spasticity, Updated Dec. 21, 2007, pp. 1-15.

Daniel P. Moore, Helping your patients with spasticity reach maximal function, vol. 104, No. 2, Aug. 1998, www.postgradmed.com/issue/1998/08_98/moore.thm., pp. 1-9.

Xencor, Product Information, Xpro-1595, (Xencor website visited Jan. 23, 2010), 3 pages.

* cited by examiner

METHOD FOR TREATING AN INTERVERTEBRAL DISC DISORDER BY ADMINISTERING A DOMINANT NEGATIVE TUMOR NECROSIS FACTOR ANTAGONIST

BACKGROUND

Tumor necrosis factor alpha (TNF α) appears early in the inflammatory cascade following infection or injury. It is produced by monocytes, macrophages, and T lymphocytes. TNF α exists as both a soluble form, solTNF, which is believed to play an important role in inflammation, and a transmembrane form, tmTNF, which is involved in immune functions.

TNF α exerts its primary effects on monocytes, synovial macrophages, fibroblasts, chondrocytes, and endothelial cells, and stimulates proinflammatory cytokine and chemokine synthesis. It activates granulocytes, and increases MHC Class II expression. It promotes secretion of matrix metalloproteinases (MMPs), leading to cartilage matrix degradation, which indicates inflammation.

Because it initiates an inflammatory cascade, and has been found to be increased in close proximity to inflamed or injured tissue, TNF α inhibition is a target for pain and/or inflammation therapy and/or tissue destruction.

Proinflammatory TNF α is expressed on the plasma membrane, and then cleaved in the extracellular domain. Trimerization of TNF α is required for biological activity. TNF α acts through two receptors (TNFRs): Type I receptors (p60, p55, CD 120a) are expressed constitutively on most cell types and Type II receptors (p80, p75, CD 120b) are inducible. Popular TNF α inhibitors act primarily to inhibit binding of TNF α to its receptors.

There are currently two major classes of TNF antagonists or blockers: (i) monoclonal antibodies to TNF α, which prevent binding of TNF α to its two cell-associated signaling receptors (p55 and p75) and (ii) monomeric soluble forms of p55 or p75 TNF receptors (TNFR) dimerized by linking them to an immunoglobulin (Ig) Fc fragment. These immunoglobulins bind to TNF α with high affinity and prevent it from binding to its cell-associated receptor.

Several TNF antagonists have been developed for systemic administration and are approved for treating various diseases of the periphery such as rheumatoid arthritis and Crohn's disease. Currently available antagonists act on soluble, extracellular TNF or TNF receptors. While these agents are effective for the above-mentioned indications, this class of TNF antagonists is associated with the risk of serious side-effects, such as opportunistic infections, immuno-suppression and demyelinating diseases.

One particular TNF antagonist that is of interest is dominant-negative TNF α (DN-TNF). This type of TNF antagonist comprises engineered variants of human TNF that do not bind to TNF receptors, but exchange subunits with native homotrimers, forming inactive heterotrimers. DN-TNF has been shown to be a specific inhibitor of solTNF, but not tmTNF, eliminating the undesirable effects of solTNF inhibitors or antibodies (such as, for example, opportunistic infections, immuno-supression and/or demyelinating diseases).

To date, however, DN-TNF has not been appreciated for treating pain and/or inflammation caused by proinflammatory cytokines, such as TNF α, associated with spinal disorders and/or osteoarthritis. Thus, there is a need to develop new methods of treating pain and/or inflammation caused by proinflammatory cytokines, such as TNF α, that are associated with spinal disorders and/or osteoarthritis.

SUMMARY

New methods are provided for treating pain and/or inflammation caused by proinflammatory cytokines, such as TNF α, that are associated with spinal disorders and/or osteoarthritis. By administering a DN-TNF locally at or near the spine or the affected osteoarthritic joint, effective treatments of pain and/or inflammation can be achieved.

In one embodiment, there is a method of treating a spinal disorder associated with a proinflammatory agent in a patient in need of such treatment, the method comprising administering an effective amount of a DN-TNF antagonist (e.g., XPro®-1595) to a target tissue site at or near the spine to reduce pain and/or inflammation. The DN-TNF antagonist can be used to treat the pain, inflammation, and/or tissue destruction from spinal disorders, such as for example, spinal cord injury, spinal cord compression, a herniated disc, a bulging disc, a collapsed disc, a degenerative disc, back pain, an inflamed nerve, sciatica, or combinations thereof.

In another embodiment, a method is provided for treating an intervertebral disc disorder associated with TNF α in a patient in need of such treatment, the method comprising administering an effective amount of a DN-TNF antagonist (e.g., XPro®-1595) to a target tissue site at or near the intervertebral disc to reduce pain, inflammation, and/or tissue destruction.

In yet another embodiment, a method is provided for treating a joint disorder associated with a proinflammatory agent in a patient in need of such treatment, the method comprising administering an effective amount of DN-TNF (e.g., XPro®-1595) to a target tissue site at or near the joint.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
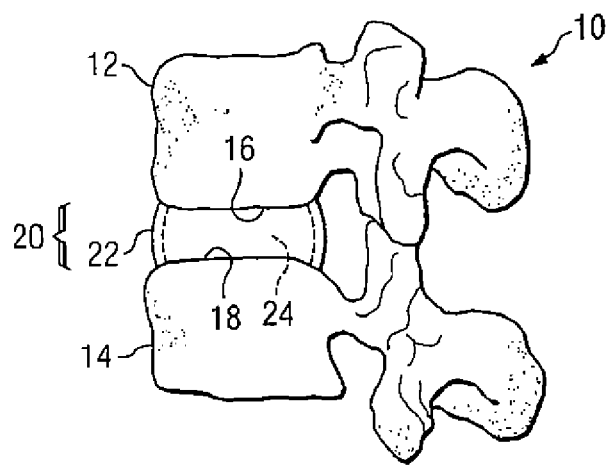
FIG. 1 illustrates a sagittal view of a section of a vertebral column that is damaged and in need of treatment.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

The term "Dominant-negative TNF α" or "DN-TNF" includes engineered variants of human TNF that do not bind to TNF receptors, but exchange subunits with native homotrimers, forming inactive heterotrimers and thus inactivate TNF α. Dominant-negative TNF α antagonists are described in U.S. Pat. No. 7,244,823 assigned to Xencor, Monrovia, California in the USA. The entire disclosure of this patent is herein incorporated by reference.

The term "XPro®-1.595" or "DN-TNF (XPro®-1.595)" refers to a dominant-negative TNF α antagonist or blocker or inhibitor of TNFα, particularly solube TNFα, XPro®-1595 is available from Xencor, Monrovia Calif. in the USA and described in col. 2, lines 23-60 and Chart 1 col. 28, line 28 to col. 29, line 15 of U.S. Pat. No. 7,244,823 assigned to Xencor, Monrovia, Calif. in the USA. The entire disclosure of this patent is herein incorporated by reference.

"Analgesic" refers to an agent or compound that can reduce, relieve or eliminate pain. Examples of analgesic agents include but are not limited to acetaminophen, a local anesthetic, such as for example, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof. Analgesic agents also include those with analgesic and anti-inflammatory properties, such as, for example, amitriptyline, carbamazepine, gabapentin, pregabalin, clonidine, or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, dictofenac, indomethacin, ibuprofen, flurbiprofen, ketoprofen, aclofenac, aloxiprin, aproxen, aspirin, diflunisal, fenoproten, mefenamic acid, naproxen, phenylbutazone, piroxicam, meloxicam; salicylamide, salicylic acid, desoxysulindac, tenoxicam; ketoralac; clonidine, flufenisal, salsalate, triethanolamine salicylate, aminopyrine, antipyrine, oxyphenbutazone, apazone, cintazone, flufenamic acid; clonixeril, meclofenamic acid, flunixin, colchicine, demecolcine, allopurinot, oxypurinol, benzydamine hydrochloride, diniefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, (enamates (metenamic acid, meclofenamic acid), naburnetone, cetecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), DN-TNF (e.g., XPro®-1595), interferons such as IL 11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; DN-TNF (e.g., XPro®-1595), sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort; desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisoiide, fluocinolone acetonide, fluocinonide; thiocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastatin (EP Appln. Publn. No. 738510A2, the entire disclosure is herein incorporated by reference), eptastatin, pitavastatin, or pharmaceutically acceptable salts thereof or a combination thereof, in various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to a drug (e.g., a DN-TNF antagonist, XPro®-1595, an anti-inflammatory agent, analgesic, or the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, p-toluenesuifortic acids, or the like.

As used herein, "disease", "disorder", "condition" and the like, as they relate to a mammal's health, are used interchangeably and have meanings ascribed to each and all of such terms.

"Treating" or "treatment of a disease or condition" refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation and/or tissue destruction. By way of example, the administration of the effective dosages of a DN-TNF antagonist (e.g., XPro®-1595) may be used to prevent, treat or relieve the symptoms of pain and/or inflammation.

"Localized" delivery includes delivery where one or more drugs are deposited within a tissue, for example, an intervertebral disc, a nucleus pulposus, an annulus fibrosis, or in close proximity (within about 5 cm, or preferably within about 2 cm, for example) thereto. A "targeted delivery system" provides delivery of one or more drugs or drug depots having a quantity of therapeutic agent that can be deposited at or near the target site as needed for treatment of pain, inflammation or other disease or condition. For example, the DN-TNF may be administered locally and the dose may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

In one embodiment, a method is provided for treating a spinal disorder associated with a proinflammatory agent in a patient in need of such treatment, the method comprising administering an effective amount of DN-TNF (e.g., XPro®-1595) to a target tissue site at or near the spine to reduce pain and/or inflammation.

DN-TNF

The anti-cytokine agent dominant-negative TNF (DN-TNF) is a TNF α binding protein and is described in Steed et al, (2003), "Inactivation of TNF signaling by rationally designed dominant-negative TNF variants", Science, 301 (5641): 1895-8. The entire disclosure is herein incorporated by reference.

DN-TNF includes engineered variants of human TNF that do not bind to TNF receptors, but exchange subunits with native homotrimers, forming inactive heterotrimers and thus inactive free TNF α. Dominant-negative TNF α antagonists are described in U.S. Pat. No. 7,244,823 assigned to Xencor, Monrovia, Calif. in the USA. The entire disclosure of this patent is herein incorporated by reference.

The DN-TNF may be administered locally in, at, or near the spine and/or osteoarthritic joint to reduce pain/and/or inflammation. In some embodiments, the DN-TNF can inhibit the production of inflammatory markers TNF α, MMP-3, nitrous oxide, IL-1 or combinations thereof. In some embodiments, the DN-TNF can inhibit the production of TNF α, MMP-3, nitrous oxide, IL-1 by 5%, 10%, 15%, 20%, 25%, 30%, 35%, 40%, 45%, 50%, 55%, 60%, 65%, 70%, 75%, 80%, 85%, 90%, 95%, 99%, or higher, particularly in vertebral cells and/or joint cells.

The term "XPro®-1595" refers to a dominant-negative TNF α antagonist or blocker or inhibitor of TNFα (DN-TNF). XPro®-1595 is available from Xencor, Monrovia Calif. in the USA and is described in col. 2, lines 23-60 and Chart 1 col. 28, line 28 to col. 29, line 15 of U.S. Pat. No. 7,244,823 assigned to Xencor, Monrovia, Calif. in the USA. The entire disclosure of this patent is herein incorporated by reference. The DN-TNF may be administered locally to spine and/or osteoarthritic joint to reduce pain/and/or inflammation and/or tissue destruction.

DN-TNF or XPro®-1595 antagonists may be administered to a patient locally to treat the pain and/or inflammation from a spinal disorder and/or osteoarthritis in an injectable composition. Injectable compositions include solutions, suspensions, dispersions, and the like. Injectable solutions or suspensions may be formulated according to techniques described in Remington's Pharmaceutical Sciences, Chapter 43, 14th Ed., Mack Publishing Co., Easton, Pa., using suitable dispersing or wetting and suspending agents, such as sterile oils, including synthetic mono- or diglycerides, and fatty acids, including oleic acid.

Solutions or suspensions comprising a therapeutic agent may be prepared in water, saline, isotonic saline, phosphate-buffered saline, and the like and may optionally be mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion either intermittent or continuous include sterile, aqueous solutions or dispersions or sterile powders comprising an active ingredient which powders are adapted for the extemporaneous preparation of sterile injectable or infusible solutions or dispersions. Preferably, the ultimate dosage form is sterile, fluid and stable under the conditions of manufacture and storage.

A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the required particle size, in the case of dispersion, or by the use of nontoxic surfactants.

The prevention of the action of microorganisms can be accomplished by various antibacterial and antifungal agents, for example, parabens, chlorobutanol, phenol, sorbic acid, thimerosal, and the like, in many cases, it will be desirable to include isotonic agents; for example, sugars, butlers, or sodium chloride. Prolonged absorption of the injectable compositions can be brought about by the inclusion in the composition of agents delaying absorption—for example, aluminum monosterate hydrogels and gelatin. Excipients that increase solubility, such as cyclodextran, may be added.

Sterile injectable solutions may be prepared by incorporating a therapeutic agent in the required amount in the appropriate solvent with various other ingredients as enumerated above and, as required, followed by sterilization. Any means for sterilization may be used. For example, the solution may be autoclaved or filter sterilized. In the case of sterile powders for the preparation of sterile injectable solutions, the preferred methods of preparation are vacuum drying and freeze-drying techniques, which yield a powder of the active ingredient plus any additional desired ingredient present in a previously sterile-filtered solution.

Dosages of a DN-TNF antagonist (e.g., XPro®-1595) may typically be decreased by at least 95% or 90% of the usual systemic oral or injectable dose if the therapeutic agent is provided locally to the target tissue site. In other embodiments, the dosage is decreased by at least 75%, at least 80% or at least 85% of the usual system oral or injectable dose for a given condition and patient population. Dosage is usually calculated to deliver a minimum amount of one or more therapeutic agent per day, although daily administration is not required. If more than one pharmaceutical composition is administered, the interaction between the same is considered and the dosages calculated.

Generally, the DN-TNF agonist or XPro®-1595 can be administered to an individual for at least 12 hours to at least a week, by injection and/or via a drug depot designed to deliver a drug for at least 1, 10, 20, 30, 100 day(s) or at least 4 months, or at least 6 months, or at least twelve to eighteen months or more, if required.

XPro®-1595 is available as a stock solution of 100 mg/ml. In some embodiments, the XPro®-1595 can be administered to the target tissue site at least 1 mcg/ml. In some embodiments, the dose of XPro®-1595 can be from 0.25 mg/kg to 20 mg/kg or 0.5 mg/kg or 10 mg/kg or 1 mg/kg to 10 mg/kg, which will result in serum levels of >1 ug/ml.

In some embodiments, the therapeutically effective dose of the DN-TNF agonist or XPro®-1595 can be delivered at such relatively low volume rates, e.g., from about 0.001 ml/day to 1 ml/day so as to minimize tissue disturbance or trauma near the site where the formulation is released. The formulation may be released at a rate of, depending on the specific biological agent(s), at a low dose, e.g., from about 0.01 mcg/hr or 0.1 mcg/hr, 0.25 mcg/hr, 1 mcg/hr, generally up to about 200 mcg/hr, or the formulation is delivered at a low volume rate e.g., a volume rate of from about 0.001 ml/day to about 1 ml/day, for example, 0.01 micrograms per day up to about 20 milligrams per day. Dosage depends on a number of factors such as potency, bioavailability, and toxicity of the respective biological agent(s).

The XPro®-1595 may be administered with TNF modulating compounds, such as for example, to enhance their activity or provide synergy to the treatment regimens. In one embodiment, the XPro®-1595 is administered before, after or with etanercept, onercept, adalimumab, anakinra, autologous blood-derived products (e.g., Orthokine, which is available from Ortho Düsseldorf Germany, infliximab or a combination thereof.

In one embodiment, the XPro®-1595 is administered before, with or after orthokine, which is an autologous preparation on human blood that results in elevated IL-1RA.

In some embodiments, the therapeutically effective dose of the DN-TNF agonist or XProe-1595 can be pegylated for sustain release delivery to the target tissue site.

Drug Depot

New methods are provided for treating pain and/or inflammation caused by proinflammatory cytokines, such as TNF α, that are associated with spinal disorders and/or osteoarthritis. By administering a DN-TNF locally at or near the spine or the affected osteoarthritic joint, effective treatments of pain and/or inflammation and/or tissue destruction can be achieved.

In one embodiment, a method is provided for treating an intervertebral disc disorder associated with TNF in a patient in need of such treatment, the method comprising administering an effective amount of a DN-TNF antagonist (e.g., XPro®-1595) to a target tissue site at or near the intervertebral disc to reduce pain and/or inflammation and/or tissue destruction. The DN-TNF antagonist (e.g., XPro®-1595) can be administered in the form of a drug depot.

A "drug depot" comprises the composition in which at least one active pharmaceutical ingredient or drug is administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot may also include a pump. The drug depot also comprises the drug itself (e.g., DN-TNF antagonist (e.g., XPro®-1595). The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API," It will be understood that unless otherwise specified a "drug" formulation may include more than one therapeutic agent, wherein exemplary combinations of therapeutic agents include a combination of two or more drugs. Thus, the drug depot may comprise DN-TNF antagonist (e.g., XPro®-1595) and an analgesic. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least DN-TNF antagonist (e.g., XPro®-1595).

A "depot" includes but is not limited to capsules, coatings, matrices, wafers, sheets, strips, ribbons, pills, pellets, microspheres, or other pharmaceutical delivery or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. Typically, the depot will be a solid or semi-solid formulation comprising a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

Suitable drug depots useful in the present application are described in U.S. Ser. No. 12,105,474 filed Apr. 18, 2008 and published as U.S. Publication No. 20090263489, and U.S. Ser. No. 12/396,122, filed Mar. 2, 2009 and published as US20090263459. The entire disclosure of these applications is incorporated by reference herein in their entirety.

The drug depot comprises a therapeutically effective amount of the DN-TNF antagonist (e.g., XPro®-1595). A "therapeutically effective amount" or "effective amount" is such that when administered, the drug results in alteration of the biological activity, such as, for example, inhibition of inflammation, reduction or alleviation of pain, improvement in the condition, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired in some embodiments the formulation containing of the drug depot containing the DN-TNF antagonist (e.g., XPro®-1595) is designed for immediate release. In other embodiments the formulation is designed for sustained release. In other embodiments, the formulation containing the DN-TNF antagonist (e.g., XPro®-1595) comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in viva of the drug depot, or a matrix or component thereof, or as the result of metabolic transformation or dissolution of the therapeutic agent(s) or conjugates of therapeutic agent(s). The continuous release does not need to be linear and can be in a continuous puke dosing fashion from the depot. As persons of ordinary skill are aware, sustained release formulations may, by way of example, be created as films, slabs, pellets, microparticles, microspheres, microcapsules, spheroids, shaped derivatives and paste. Further, the formulations may be used in conjunction with any implantable, or insertable system that a person of ordinary skill would appreciate as useful in connection with embodiments herein including but not limited to parenteral formulations, microcapsules, pastes, implantable rods, pellets, plates or fibers, etc.

The DN-TNF antagonist (e.g., XPro®-1595) may be in an immediate release formulation. The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1, 2, 3, 4, 5, 6, 7, 8, 9, 10, 11, or 12 hours. The immediate release formulation provides relief of pain and/or inflammation within 24 hours or sooner.

The depot can be designed to provide the desired release rate profile for immediate release and/or sustained release of the DN-TNF antagonist (e.g., XPro®-1595). The phrase "release rate profile" refers to the percentage of active ingredient that is released over fixed units of time, e.g., mcg/hr, mcg/day, mg/hr, mg/day, 10% per day for ten days, and the like. As persons of ordinary skill know, a release rate profile may be but need not be linear. By way of a non-limiting example, the drug depot may be a pellet that releases at least the DN-TNF antagonist (e.g., XPro®-1595) in a bolus dose and at least the DN-TNF antagonist (e.g., XPro®-1595) over an extended period of time.

The depot can be biodegradable. The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The depot may comprise non-biodegradable material. Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl airlines, polyvinyl pyridine, and polyvinyl imidazole. Depending on the amount of crosslinking within the bioresorbable polymers, the degradation time of the polymer can be reduced, thus making the polymer, for the purpose of this invention, appear to be non-resorbable over the time frame of the use of the material for this invention.

The DN-TNF antagonist (e.g., XPro®-1595) can provide the appropriate pain management medication. The phrase "pain management medication" includes one or more therapeutic agents that are administered to prevent, alleviate or remove pain entirely. These include anti-inflammatory agents, analgesics, anesthetics, narcotics, and so forth, and combinations thereof.

In various embodiments, the depot can be designed to cause an initial burst dose of one or more therapeutic agents (e.g., DN-TNF antagonist (e.g., XPro®-1595) within the first 24 hours after implantation. "Initial burst" or "burst effect" or "bolus dose" or "pulse dose" refer to the release of therapeutic agent from the depot during the first 24 hours after the depot comes in contact with an aqueous fluid (e.g., synovial fluid, cerebral spinal fluid, etc.). The burst effect may be an immediate release. The "burst effect" is believed to be due to the increased release of therapeutic agent from the depot. The initial burst effect or bolus dose may be determined beforehand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region or depot, in various embodiments, can be designed so that a larger initial dose may be released over a short period of time to achieve the desired effect. For example, if a drug depot is designed to release 15 mg of DN-TNF antagonist (e.g., XPro®-1595) per 48 hours, then the initial burst dose or bolus dose region or depot will be designed to release a percentage of the dose within the first 24 hours (e.g., 10 mg of DN-TNF antagonist or 66% of the 48 hour dose within 24 hours). Thus, the burst effect of the drug depot or region releases more therapeutic agent than the sustained release region or depot.

A region or depot that utilizes a burst effect or bolus dose will release more therapeutic agent (e.g., DN-TNF antagonist (e.g., XPro®-1595)) than the sustained release region or depot. For example, particularly with painful conditions such as discogenic back pain, or the like, the initial burst effect of the drug depot or region of the drug depot will be advantageous as it will provide more immediate pain and/or inflammation and/or tissue destruction relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation and/or tissue destruction.

In some embodiments, the drug depot may have an initial burst effect to release the drug shortly after it is implanted. Various factors can be adjusted to achieve the initial burst of therapeutic agent release. First, the initial burst can be controlled by factors related to the property of the depot, such as the water immiscibility of the solvent, polymer/solvent ratio, and the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a tower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

The drug depot may comprise DN-TNF antagonist (e.g., XPro®-1595) and at least one analgesic agent or its pharmaceutically acceptable salt. Examples of analgesic agents include but are not limited to acetaminophen, a local anesthetic, such as for example, lidocaine, bupivacaine, ropivacaine, and non-opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof. Analgesic agents also include those with analgesic and anti-inflammatory properties, such as, for example, amitriptyline, carbamazepine, gabapentin, pregabalin; clonidine, or a combination thereof.

The drug depot can comprise DN-TNF antagonist (e.g., XPro®-1595) and at least one analgesic agent or its pharmaceutically acceptable salt and/or at least one anti-inflammatory agent or its pharmaceutically acceptable salt that may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the DN-TNF antagonist (e.g., XPro®-1595). Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), mAb (Critical Therapeutics Inc.), anti-IL2R antibodies (daclizumab, basilicimab), ABX (anti IL-8 antibodies), recombinant human IL-10, or HuMax IL-15 (anti-IT 15 antibodies).

Other suitable therapeutic agents that may be co-administered or part of the DN-TNF antagonist (e.g., XPro®-1595) formulation include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1, or Orthokine® which is an autologous preparation of activated serum with high concentration of IL-RA. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dithiocarbamate.

Specific examples of additional therapeutic agents suitable for use include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

For each of analgesic agent or anti-inflammatory agent including DN-TNF antagonist (e.g., XPro®-1595) in the depot, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

The drug depot may also be administered with non-active ingredients. These non-active ingredients may have multifunctional purposes including the carrying, stabilizing and controlling the release of the therapeutic agent(s). The sustained release process, for example, may be by a solution-diffusion mechanism or it may be governed by an erosion-sustained process.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation of the drug depot can occur either at the surface (heterogeneous or surface erosion) or uniformly throughout the drug depot (homogeneous or bulk erosion).

In various embodiments, the depot may comprise a bioabsorbable, and/or a biodegradable biopolymer that may provide immediate release, or sustained release of the DN-TNF antagonist (e.g., XPro®-1595). Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumins, fibrin, vitamin E analogs, such as alpha tocopheryl acetate, d-alpha tocopheryl succinate, D,L-actide, or L-lactide, poly(glycolide-, -caproiactone), -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (b, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dl/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly (orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the DN-TNF antagonist XPro®-1595) are the only components of the pharmaceutical formulation.

In some embodiments, at least 75% of the particles in the depot have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenyls acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material.

The depot can be different sizes, shapes and configurations, such as for example, strip, rod, sheet, mesh, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

Spinal Disorders

In one embodiment, there is a method of treating a spinal disorder associated with a proinflammatory agent in a patient in need of such treatment, the method comprising administering an effective amount of DN-TNF antagonist (e.g., XPro®-1595) to a target tissue site at or near the spine to reduce pain and/or inflammation. The DN-TNF antagonist (e.g., XPro®-1595) can be used to treat the pain and/or inflammation from spinal disorders, such as for example, spinal cord injury, spinal cord compression, a herniated disc, a bulging disc, a collapsed disc, a degenerative disc, back pain, inflamed nerve, sciatica, or combinations thereof.

Spinal disorders include any disease or conditions related to the spine or tissue in or surrounding the spine. Spinal disorders include back pain, disc herniation, or bulging disc, internal disc disruption or fissured discs, a collapsed disc, a compressed disc, a degenerative disc, an inflamed nerve, radiculopathy, spinal stenosis, herniated nucleus pulposus-induced sciatica, sciatica, spinal cord injury, spinal cord compression, idiopathic scoliosis, spondylolisthesis, retrolisthesis or, facet pain, facet degeneration, bone fractures, vertebral compression fractures, or myelopathy.

One spinal disorder that the DN-TNF antagonist XPro®-1595) can be used to treat includes degeneration of the intervertebral disc (IVD). IVD is a multifactoral process involving mechanical, genetic and biological factors. Although the pathophysiological mechanism remains unclear, resultant changes in structure and function of the disc have been well described. Unlike articular cartilage, the IVD is composed of different tissues. The healthy IVD is a well-encapsulated, avascular organ which contains a jelly-like nucleus pulposus (NP) surrounded by a fibrous annulus fibrosus (AF), which provides mobility and a cushion between the vertebrae. The nucleus pulposus is located at the center of each disc and is composed of chondrocytes which produce an extracellular matrix containing a high percentage of proteoglycans (PG) and type II collagen in the adult. The nucleus pulposus is surrounded by the annulus fibrosus which consists of highly organized, directionally oriented collagen fibers oriented in concentric lamellae, and extracellular matrix. The inner annulus fibrosus is thicker than the outer and has a fibrocartilaginous matrix that lacks the lamellar structure. A thin distinct region, the transition zone (TZ), divides the inner annulus from the nucleus pulposus.

During the aging process, the reduction in proteoglycan content of the nucleus leads to decreased hydration and evidence of degeneration, including reduction in disc height and increased load on the surrounding structures of the spine.

At the biological level it reflects an imbalance between the normal anabolic and catabolic function of the nucleus pulposus cells. In some cases of degenerative disc disease (DDD), gradual degeneration of IVD is caused by mechanical instabilities. Increased load and pressure on the nucleus pulposus cause the cells or invading macrophages to produce larger amounts of cytokines or toxic amounts of metalloproteinases (MMPs). As DDD progresses, toxic levels of cytokines and MMPs degrade the extracellular matrix and lead to a destruction of the proteoglycans, thereby reducing the water-retaining capabilities with resulting dehydration of the nucleus pulposus. Following this, the flexibility of the nucleus pulposus is reduced and delamination of the annulus fibrosus might be the consequence, eventually developing internal fissures spreading out towards the periphery. These alterations cause even more mechanical instability and induction of cytokine production, which progress the DDD and the disc begins to bulge (herniated disc disease) and ultimately ruptures, with nerve irritation and lower back pain.

The term "degenerative disc disease (DDD)" is a chronic process characterized in part by progressive loss of proteoglycan and water content in the nucleus pulposus that can become manifest in multiple disorders such as idiopathic low back pain, disc herniation, internal disc disruption or fissured discs, radiculopathy, spinal stenosis, herniated nucleus pulposus-induced sciatica, sciatica, idiopathic scoliosis and/or myelopathy. The disc degeneration grade can be ranked by analysis of preoperative MRI.

In some embodiments, a method is provided for treating an intervertebral disc disorder associated with TNF α in a patient in need of such treatment, the method comprising administering an effective amount of a DN-TNF antagonist (e.g., XPro®-1595) to a target tissue site at or near the intervertebral disc to reduce pain and/or inflammation. In some embodiments, the DN-TNF (e.g., XPro®-1595) is administered locally at, near, or in the facet joint, annulus fibrosus, or the nucleus pulposus of the spine.

In one embodiment, the DN-TNF antagonist (e.g., XPro®-1595) can be used to treat pain and/or inflammation from sciatica. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the DN-TNF antagonist (e.g., XPro®-1595) may be used to reduce, treat, or prevent sciatic pain and/or inflammation by locally administering the DN-TNF antagonist (e.g., XPro®-1595) at one or more target tissue sites (e.g., nerve root, dorsal root ganglion, focal sites of pain, at or near the spinal column, etc.).

In one embodiment, DN-TNF antagonist XPro®-1595) as discussed above is implanted locally at or near the target tissue site (e.g., at or near the spine or within 5 cm or less of it) affected with the spinal disorder so that the drug depot releases an effective amount of DN-TNF antagonist (e.g., XPro®-1595) as discussed above to reduce, prevent or treat the spinal disorder. The drug depot may release the DN-TNF antagonist (e.g., XPro®-1595) over a period of 1-90 days, 1-10 days, 1-3 days, 3-7 days, 3-12 days; 3-14 days, 7-10 days, 7-14 days, 7-21 days, 7-30 days, 7-50 days, 7-90 days, 7-120 days, 7-140 days, 14-140 days, 3 days to 135 days, 3 days to 150 days, or 3 days to 6 months. In some embodiments, one or more drug depots containing the DN-TNF antagonist (e.g., XPro®-1595) can be implanted in one or more of the same or separate procedures.

In some embodiments, DN-TNF antagonist (e.g., XPro®-1595) can be administered to treat facet pain or facet degeneration and the agent can be administered at or near the facet joint to treat pain, inflammation, and/or tissue destruction. This treatment will be particularly useful for back pain.

In some embodiments, the drug depot may release the DN-TNF antagonist (e.g., XPro®-1595) over a period of 1-90 days, 1-10 days, 1-3 days, 3-7 days, 3-12 days; 3-14 days, 7-10 days, 7-14 days, 7-21 days, 7-30 days, 7-50 days, 7-90 days, 7-120 days, 7-140 days, 14-140 days, 3 days to 135 days, 3 days to 150 days, or 3 days to 6 months. In some embodiments, one or more drug depots containing the DN-TNF antagonist (e.g., XPro®-1595) can be implanted in one or more of the same or separate procedures.

Osteoarthritis

In one embodiment, a DN-TNF antagonist (e.g., XPro®-1595) is provided useful for reducing, preventing or treating pain and/or inflammation from osteoarthritis in a patient in need of such treatment. DN-TNF antagonist (e.g., XPro®-1595) can be contained in an implantable drug depot and the drug depot being implantable at a site beneath the skin or gum to reduce, prevent or treat pain and/or inflammation from osteoarthritis, wherein the drug depot is capable of releasing an effective amount of the XPro®-1595 over a period of at least one day As used herein, "osteoarthritis" refers to a particular form of arthritis, and in particular a chronic disease in which the articular cartilage that lies on the ends of bones that form the articulating surface of the joints gradually degenerates over time.

Osteoarthritis is one of the most widespread forms of degenerative joint and bone diseases. The exact cause of osteoarthritis is unknown at this time; however, the entire process is thought to involve a complex interaction of cells and soluble mediators such as cytokines, growth factors, inflammatory mediators, metalloproteinases, and chondro-degradative enzymes. This complex interaction may further be triggered by physical trauma, surgery, infection, or another disease process. In its more advanced stages, osteoarthritis is characterized by fraying and fibrillation of cartilage resulting from the elaboration of proteolytic and collagenolytic enzymes by the chondrocytes that initially attack the joint matrix. Inflammation of the synovial tissue develops and leads to an increase of cytokines that attack the cartilage. The synovitis also leads to an increase in edema, vascularity and severe pain in the joint.

The disease progression may range from relatively mild symptoms causing pain and swelling to extreme debilitation and physical incapacitation. Complete destruction of the cushioning tissue in the joints may also lead to bone erosion and required joint replacement. Osteoarthritis is a disease that affects all ages, but is more strongly pronounced among and highly prevalent in people 45 and older.

In one embodiment, DN-TNF antagonist (e.g., XPro®-1595) as discussed above is implanted locally at or near the target tissue site (e.g., within the joint or within 5 cm or less of it) affected with the osteoarthritis so that the drug depot releases an effective amount of DN-TNF antagonist (e.g., XPro®-1595) as discussed above to reduce, prevent or treat osteoarthritis. The drug depot may release the XPro®-1595 over a period of 1-90 days, 1-10 days, 1-3 days, 3-7 days, 3-12 days; 3-14 days, 7-10 days, 7-14 days, 7-21 days, 7-30 days, 7-50 days, 7-90 days, 7-120 days, 7-140 days, 14-140 days, 3 days to 135 days, 3 days to 150 days, or 3 days to 6 months. In some embodiments, one or more drug depots containing the DN-TNF antagonist (e.g., XPro®-1595) can be implanted in one or more of the same or separate procedures.

Gene Therapy

Advances in the field of gene therapy now make it possible to introduce into cells the DNA sequence encoding DN-TNF antagonist (e.g., XPro®-1595). Gene therapy offers a number of potential advantages: (1) lower production costs; (2) greater efficacy, compared to extracellular treatment regimens, due to the ability to achieve prolonged expression of the DN-TNF antagonist (e.g., XPro®-1595); and (3) it permits the delivery of transfected DN-TNF antagonist (e.g., XPro®-1595) cells directly to the site where treatment is needed.

Ex vivo transfection of cells and stem cells (e.g., pluripotential stem cells or mesenchymal stem cells) with the nucleic acid sequence that encodes a DN-TNF antagonist (e.g., XPro®-1595), followed by reimplantation of the transfected cells in the donor, is suitable for treating a variety of the above described disorders or injuries. For example, one can use this method to inhibit pain, inflammation, and/or tissue destruction from a spinal disorder, fracture, and/or osteoarthritis.

In addition to ex vivo methods of gene therapy, transfection of a recombinant DNA vector comprising a nucleic acid sequence that encodes a DN-TNF antagonist (e.g., XPro®-1595) can be accomplished in vivo. When a DNA fragment that encodes a DN-TNF antagonist (e.g., XPro®-1595) is inserted into an appropriate viral vector, for example, an adenovirus vector, the viral construct can be injected directly into a body site where the anti-inflammatory effect is desired.

By using a direct, percutaneous injection to introduce the DNA sequence that encodes a DN-TNF antagonist XPro®-1595), the desired effect can be accomplished without the need for surgical intervention.

It is also possible to carry out in vivo gene therapy by directly injecting into an appropriate body site, a naked, that is, unencapsulated, recombinant plasmid comprising a nucleic acid sequence that encodes a DN-TNF antagonist (e.g., XPro®-1595). In this embodiment, transfection occurs when the naked plasmid DNA is taken up, or internalized, by the appropriate target cells. As in the case of in vivo gene therapy using a viral construct, direct injection of naked plasmid DNA offers the advantage that little or no surgical intervention is required.

For intervertebral disc applications, ex vivo transfection may be accomplished by harvesting cells from an intervertebral disc, transfecting the cells with nucleic acid encoding a DN-TNF antagonist (e.g., XPro®-1595) in vitro, followed by introduction of the cells into an intervertebral disc. The cells may be harvested from or introduced back into the intervertebral disc using any means known to those of skill in the art, such as, for example, any surgical techniques appropriate for use on the spine. In one embodiment, the cells are introduced into the intervertebral disc by injection.

In some embodiments, stem cells (e.g., pluripotential stem cells or mesenchymal stem cells) can be transfected with nucleic acid encoding a DN-TNF antagonist (e.g., XPro®-1595) ex vivo and introduced into the intervertebral disc (e.g., by injection).

The cells transfected ex vivo can also be combined with a carrier to form an intervertebral disc implant. The carrier comprising the transfected cells can then be implanted into the intervertebral disc of a subject. Suitable carrier materials are disclosed in Helm, et al. "Bone Graft Substitutes for the Promotion of Spinal Arthrodesis", Neurosurg Focus, 10 (4) (2001). In some embodiments, the carrier comprises a biocompatible porous matrix such as a demineralized bone matrix (DBM), a biocompatible synthetic polymer matrix or a protein matrix. Suitable proteins include extracellular matrix proteins such as collagen. The cells transfected with the DNA encoding a DN-TNF antagonist (e.g., XPro®-1595) ex vivo can be incorporated into the carrier (i.e., into the pores of the porous matrix) prior to implantation.

Similarly, for intervertebral disc applications where the cells are transfected in vivo, the DNA may be introduced into the intervertebral disc using any suitable method known to those of skill in the art. In one embodiment, the nucleic acid is directly injected into the intervertebral space.

Cannula or Needle

The drug, drug depot can be loaded in a cannula or needle that is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey, in various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation in various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments, the plunger, cannula, drug, and/or drug depot can include markings that indicate location at or near the site beneath the skin. Radiographic markers can be included to permit the user to accurately position the cannula, drug, and/or drug depot into the site of the patient. These radiographic markers will also permit the user to track movement and degradation of the drug, drug depot at the site over time. In this embodiment, the user may accurately position the drug, drug depot, cannula in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

Administration

In various embodiments, the DN-TNF antagonist (e.g., XPro®-1595) is administered locally at or near an intervertebral to reduce or prevent pain and/or inflammation, in various embodiments, the DIN-TNF antagonist may be parenterally administered. The term "parenteral" as used herein refers to modes of administration, which bypass the gastrointestinal tract, and include for example, intramuscular, intraperitoneal, intrasternal, subcutaneous, intra-operatively, intrathecally, intradiskally, peridiskally, epidurally, perispinally, intradiscally, peridiskally, intraarticular or combinations thereof. Parenteral administration also includes an infusion pump that administers a pharmaceutical composition through a catheter near the target site, an implantable mini-pump that can be inserted at or near the target site, and/or an implantable controlled release device or sustained release delivery system that can release a certain amount of the composition per hour or in intermittent bolus doses.

One example of a suitable pump for use is the SynchroMed® (Medtronic, Minneapolis, Minn.) pump. The pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals.

Potential drug delivery devices suitable for adaptation for the methods described herein include but are not limited to those described, for example, in U.S. Pat. No. 6,551,290 (assigned to Medtronic, the entire disclosure of which is herein incorporated by reference), which describes a medical catheter for target specific drug delivery; U.S. Pat. No. 6,571,125 (assigned to Medtronic, the entire disclosure of which is herein incorporated by reference), which describes an implantable medical device for controllably releasing a biologically active agent; U.S. Pat. No. 6,594,880 (assigned to Medtronic, the entire disclosure of which is herein incorporated by reference), which describes an interparenchymal infusion catheter system for delivering therapeutic agents to selected sites in an organism; and U.S. Pat. No. 5,752,390 (assigned to Medtronic, the entire disclosure of which is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, lightweight devices for delivering liquid medication, implantable micro-miniature infusion devices, implantable ceramic valve pump assemblies, or implantable infusion pumps with a collapsible fluid chamber. Atzett osmotic pumps (Durect Corporation, Cupertino, Calif.) are also available in a variety of sizes, pumping rates, and durations suitable for use in the described methods.

In various embodiments, because the DN-TNF antagonist (e.g., XPro®-1595) is locally administered, therapeutically effective doses may be less than doses administered by other routes (oral, topical, etc), in turn, systemic side effects, such as for example, liver transaminase elevations, hepatitis, liver failure, myopathy, constipation, etc, may be reduced or eliminated. The DN-TNF antagonist XPRO®-1595) can be delivered to any site beneath the skin, including, but not limited to, at least one muscle, ligament, tendon, cartilage, spinal disc, spinal foraminal space, near the spinal nerve root, or spinal canal.

In some embodiments, a method of treating a nucleus pulposus within an annulus fibrosis in a patient in need of such treatment is provided, the method comprising administering the DN-TNF antagonist (e.g., XPro®-1595) at or near the annulus fibrosis to reduce or inhibit pain and/or inflammation over a period of at least one day.

Referring to FIG. 1, the reference numeral 10 refers to a vertebral joint section or a motion segment of a vertebral column. The joint section 10 includes adjacent vertebral bodies 12 and 14. The vertebral bodies 12 and 14 include endplates 16 and 18, respectively. An intervertebral disc space 20 is located between the endplates 16, and 18, and an annulus fibrosis 22 surrounds the space 20 and holds a nucleus pulposus 24.

Figure 2:
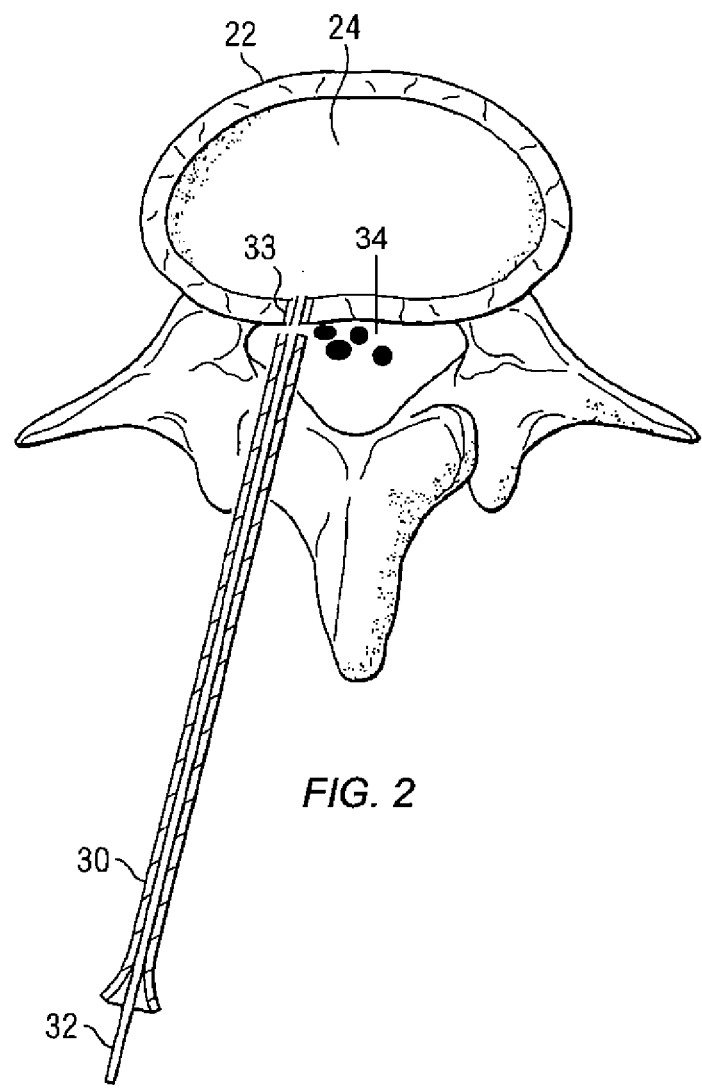
FIG. 2 illustrates an embodiment of an intervertebral disc treatment including administering a drug depot containing DN-TNF (e.g., XPro®-1595) through a needle or cannula at or near the annulus fibrosis, which has been damaged.

Referring now to FIG. 2, in this embodiment, an annular tear 33 is present that nucleus pulposus 24 can herniated out this tear in the embodiments of the present application, a DN-TNF antagonist (e.g., XPro®-1595) is locally delivered next to the annulus fibrosis of the disc and next to the tear 33 by inserting a cannula 30 into the patient and locating the cannula at or near the annulus 22 and delivering a plurality of depots 34 containing a DN-TNF antagonist (e.g., XPro®-1595) to the target tissue site. The DN-TNF antagonist XPro®-1595) can be delivered by coupling a syringe containing this agent to port 32. The DN-TNF antagonist (e.g., XPro®-1595) will be released over a period of time of at least 24 hours to relieve the pain and/or inflammation.

Figure 3:
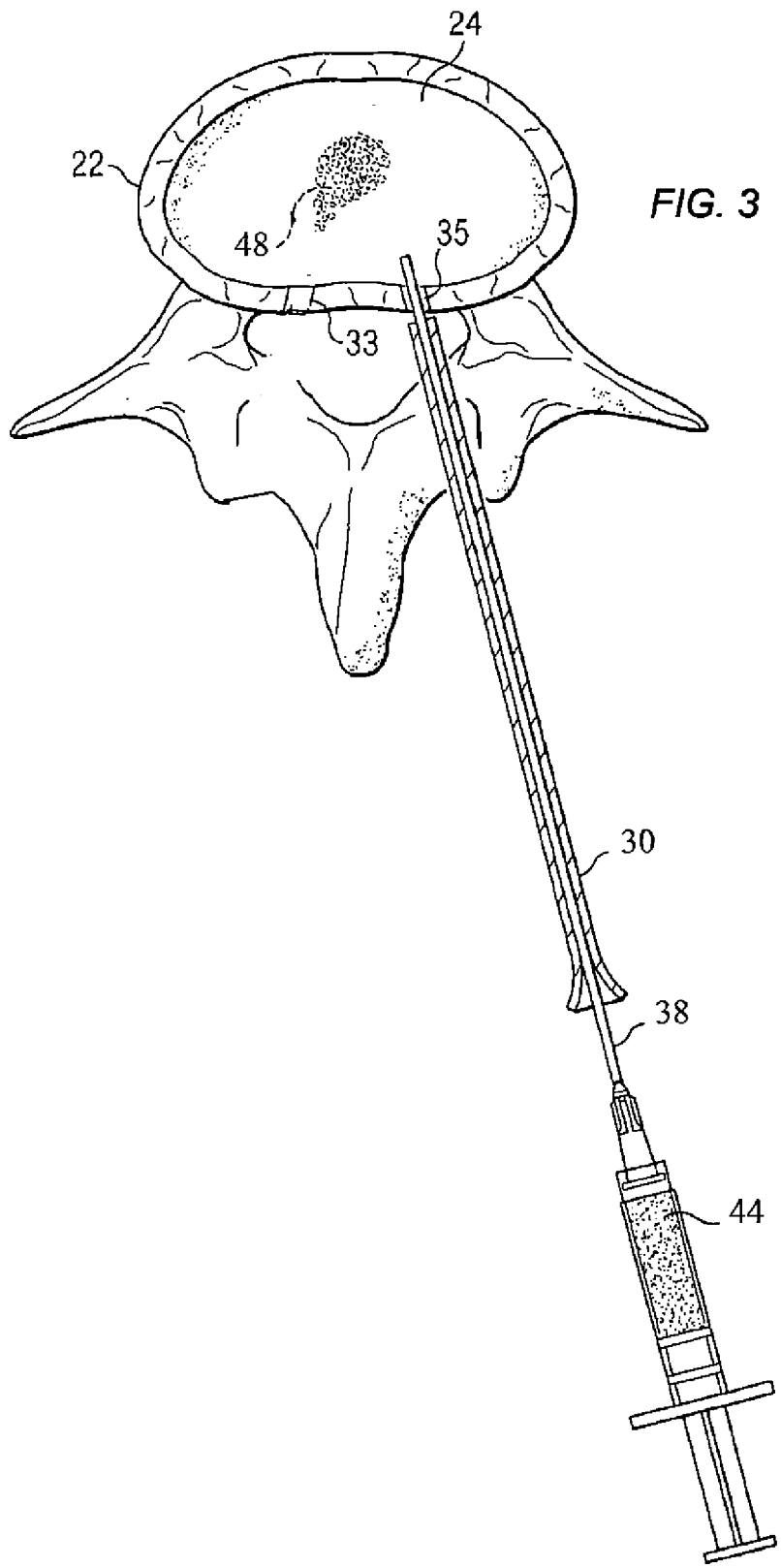
FIG. 3 illustrates an embodiment of an intervertebral disc treatment including administering a DN-TNF liquid (e.g., XPro®-1595) locally directly in the nucleus pulposus of the intervertebral disc.

Referring now to FIG. 3, in this embodiment, an annular tear 33 is present and the nucleus pulposus 24 has left the disc space from this tear. Therefore, the disc needs treatment for the pain and/or inflammation associated therewith. In the embodiments of the present application, a DN-TNF antagonist (e.g., XPro®-1595) is locally delivered to the nucleus pulposus 24 by introducing a catheter 30 into a region 35 next to tear 33 in the annulus fibrosis 22 and delivering a DN-TNF antagonist (e.g., XPro®-1595) 48 into the nucleus pulposus 24. The DN-TNF antagonist (e.g., XPro®-1595) will block inflammatory cytokines (e.g., TNF α). The DN-TNF antagonist (e.g., XPro®-1595) can be delivered to the disc space by coupling a syringe 44 containing the DN-TNF antagonist 44 (e.g., XPro®-1595) to port 38 and injecting it into the target tissue site. In some embodiments, the practitioner can create the hole 35 in the annulus fibrosis of the disc and next to the tear 33 by inserting a cannula 30 into the patient and locating the cannula through annulus 22 by hole 35 and delivering the DN-TNF antagonist 48 (e.g., XPro®-1595) to the target tissue site. The DN-TNF antagonist (e.g., XPro®-1595) can be delivered by coupling a syringe containing this agent to port 38. The DN-TNF antagonist (e.g., XPro®-1595) can be a sustained release formulation (e.g., liquid, powder, depot, etc.) that will provide long term relief to the patient of the pain and/or inflammation. In this embodiment, the nucleus is accessed using a posterior bilateral approach. In alternative embodiments, the annulus may be accessed with a lateral approach, an anterior approach, a trans-pedicular/vertebral endplate approach or any other suitable nucleus accessing approach. Although a bilateral approach is described, a unilateral or multi-lateral approach may be suitable.

In some embodiments, the therapeutically effective dosage amount and the release rate profile of the DN-TNF antagonist (e.g., XPro®-1595) are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, or 14-140 days.

In some embodiments, the DN-TNF antagonist (e.g., XPro®-1595) is administered as a bolus dose at the target tissue to provide an immediate release. Such doses can be given by single or multiple injections, or via pump as a continuous infusion or by pulse dosing via an infusion pump or an implantable pump or depot.

In some embodiments, there is a composition useful for the treatment of pain and/or inflammation comprising an effective amount of the DN-TNF antagonist (e.g., XPro®-1595) and another therapeutic agent (e.g., analgesic agent, anti-inflammatory agent, etc.) that is capable of being administered to e.g., a pain or inflammatory site. By way of example, they may be administered locally to the foraminal spine, paraspinal muscles or subcutaneous tissues.

In some embodiments, a plurality of depots containing the DN-TNF antagonist (e.g., XPro®-1595) can be placed around the disc to provide a strategy to triangulate around the pain generator. A strategy of triangulation may be effective when administering multiple depot pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the drug depot is implantable at or near a target tissue site at the time of surgery. The active ingredients may then be released from the depot via diffusion in a sustained fashion over a period of time, e.g., 1-3 days, 3-15 days, 5-40 days or 7-10 days post surgery in order to address pain and inflammation.

In some embodiments, a desired release rate profile is maintained for at least three days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days.

In some embodiments, the drug depot may release 5%, 10%, 15%, 20%, 25%, 30%, 40%, 50%, 60%, 70%, 80%, 90%, 95%, or 99% of the DN-TNF antagonist (e.g., XPro®-1595) relative to a total amount of the DN-TNF antagonist (e.g., XPro®-1595) loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days. In various embodiments, the DN-TNF antagonist (e.g., XPro®-1595) will be released in an initial burst dose, then the DN-TNF antagonist (e.g., XPro®-1595) will be released daily without a burst dose for 3 to 12 days, 5 to 10 days or 7 to 10 days after the drug depot is administered to the target tissue site.

In various embodiments, a kit is provided comprising one or more drug depots (containing the immediate release and/or sustained release DN-TNF antagonist (e.g., XPro®-1595). The kit may include additional parts along with the drug depot and/or medical device combined together to be used to implant the drug depots (e.g., pellets, strips, meshes etc.). The kit may include the drug depot delivery device in a first compartment. The second compartment may include a canister holding the drug depots and any other instruments needed for the localized drug delivery. A third compartment may include gloves, drapes, needles, wound dressings and other procedural supplies for maintaining sterility of the implanting process, as well as an instruction booklet. A fourth compartment may include additional needles and/or sutures. Each tool may be separately packaged in a plastic pouch that is radiation sterilized, A fifth compartment may include an agent for radiographic imaging. A cover of the kit may include illustrations of the implanting procedure and a clear plastic cover may be placed over the compartments to maintain sterility.

Method of Making Drug Depot

In various embodiments, the drug depot comprising the active ingredients (e.g., DN-TNF antagonist (e.g., XPro®-1595) can be made by combining a biocompatible polymer and a therapeutically effective amount of the active ingredients or pharmaceutically acceptable salts thereof and forming the implantable drug depot from the combination.

Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., the DN-TNF antagonist), in various embodiments, the PGLA or PLA can be premixed with the radio-opacifying agent at temperatures of about, for example, slightly above room temperature. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 35° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where water-soluble therapeutic agents are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Thus, a sustained release region of the drug depot may, in various embodiments, be made by immediately removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of DN-TNF antagonist (e.g., XPro®-1595) and forming the implantable drug depot from the combination.

Having now generally described the invention, the same may be more readily understood through the following reference to the following examples, which are provided by way of illustration and are not intended to limit the present invention unless specified.

EXAMPLES

Introduction

The intervertebral disc (IVD), under pathological conditions such as herniation or degeneration, has been shown to express increased levels of the proinflammatory cytokines, interleukin-1 (IL-1) and its regulator, tumor necrosis factor-α (TNF-α). TNF plays a role in mediating the pain caused by nerve root compression associated with herniated discs. Recently, the application of anti-TNF antibodies has been used to treat pain in patients with herniated discs. The autocrine production of cytokines is considered to be one of the key regulatory mechanisms of cartilage metabolism. TNF-α has also been shown to induce the suppression of proteoglycan synthesis and the production of matrix-degrading enzymes. Because some cytokines, such as IL-1, induce TNF production, cytokine inhibitors that block the TNF-α pathway may alter the accelerated catabolic rate induced by these cytokines in pathological discs by blocking the effects of TNF-α produced in an autocrine and/or paracrine fashion.

TNF exists as both a soluble form, solTNF, which is believed to play an important role in inflammation, and a transmembrane form, tmTNF, which is involved in immune functions. Dominant-negative TNF-α (DN-TNF) is comprised of engineered variants of human TNF that do not bind to TNF receptors, but exchange subunits with native homotrimers, forming inactive heterotrimers. DN-TNF has been shown to be a specific inhibitor of solTNF, but not tmTNF, eliminating the undesirable effects of solTNF inhibitors or antibodies.

The aim of this study was to investigate the effects of a novel TNF-α inhibitor, DN-TNF (XPro®-1595) on the catabolic activity of human primary IVD cells cultured in alginate beads.

Materials and Methods

Cell Preparation: Human nucleus pulposus (NP) and annulus fibrosus (AF) cells isolated from cadaveric IVD tissues (three separate donors; Thrompson grades 2-3; mean age, 61-years old) were cultured in 1.2% alginate for 7 days in DMEM/F12/10% fetal bovine serum (FBS)/ascorbate.

Effect of DN-TNF on the catabolic activity of human IVD cells were serum-starved overnight and then treated for 48 hrs with one of the following conditions: 1) control (DMEM/F12); 2) IL-1β (10 ng/mL); 3) (DN-TNF, [XPro® 1595], 0.1, 1 and 10 ng/mL; provided by Medtronic Spinal and Biologics, Sunnyvale, Calif.), or 4) IL-1β (10 ng/mL)+DN-TNF (0.1, 1 and 10 ng/mL). After 48 hours, total nitrite (the Nitric Oxide Metabolite Detection Kit; Cayman, Mich.), TNF-α (Human TNF-alpha ELISA high sensitivity; e-Bioscience. CA), and MMP-3 (MMP-3 ELISA kit; Biosource, CA) released into the media were assessed.

Results

Figure 4:
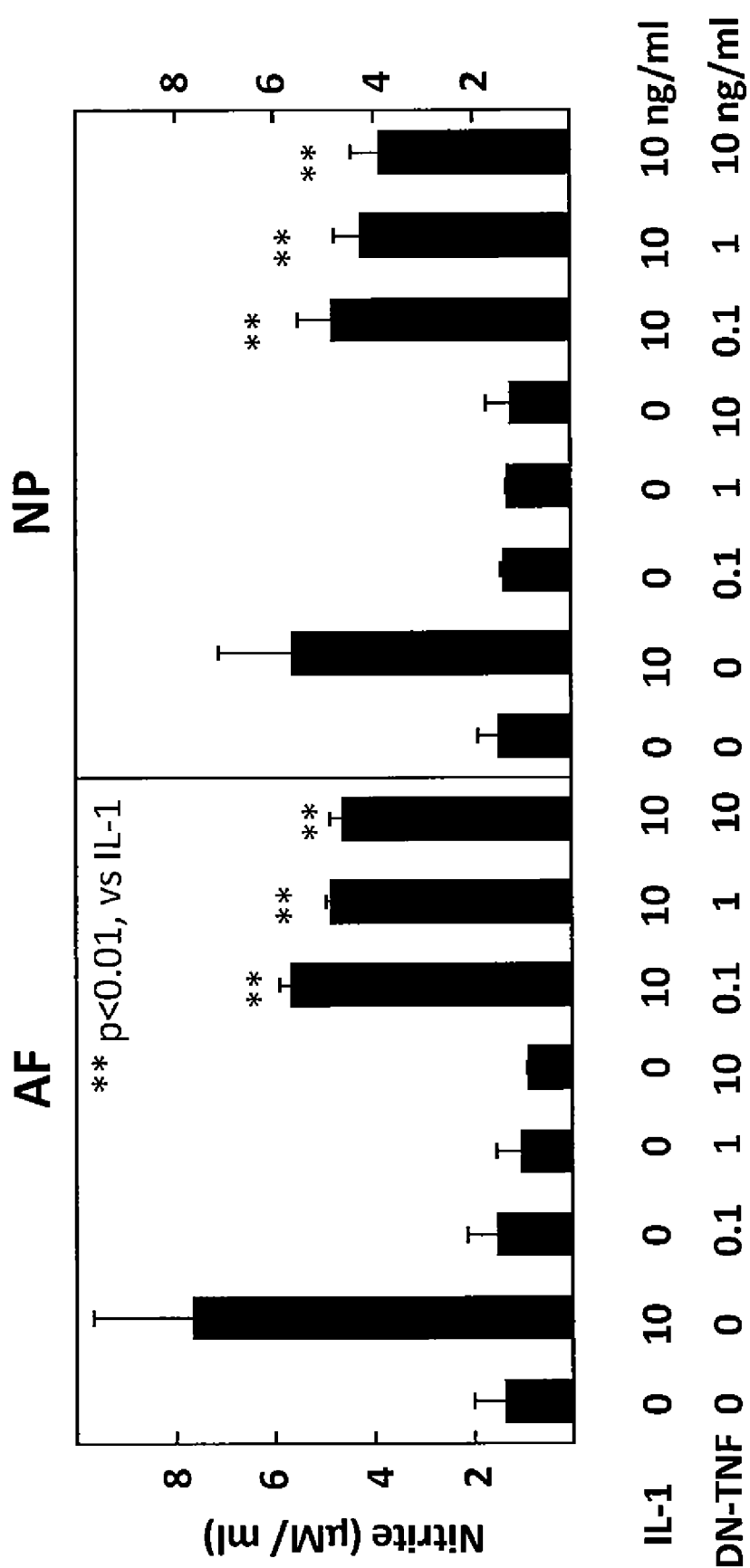
FIG. 4 is a bar graph illustration showing that IL-1β significantly stimulated the release of nitrites in human intervertebral disc cells and that the addition of DN-TNF XPRO®-1595) at 10 ng/mL into the culture media containing the disc cells significantly suppressed nitrites marker (an inflammatory marker).
Figure 5:
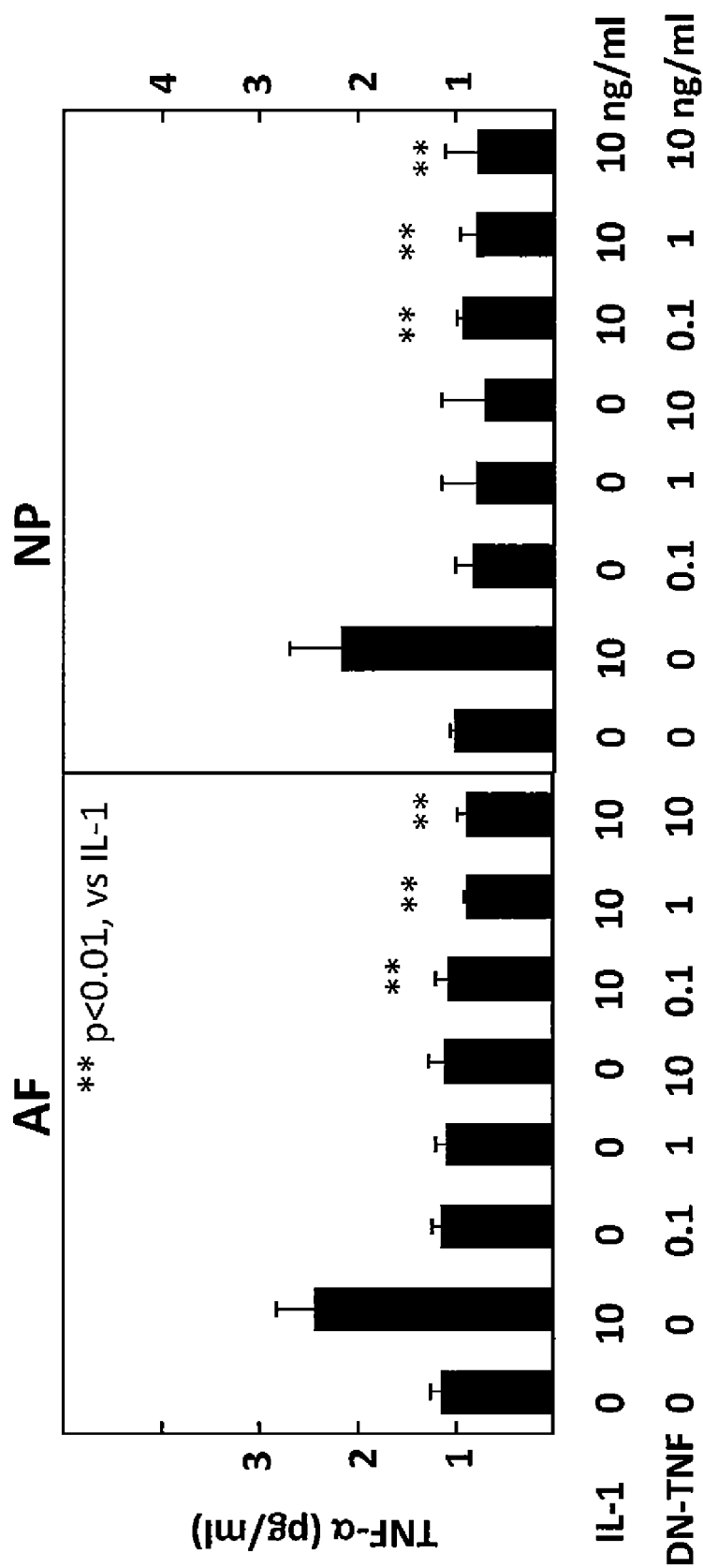
FIG. 5 is a bar graph illustration showing that IL-1β significantly stimulated the release of TNF-α in human intervertebral disc cells and that the addition of DN-TNF (e.g., XPRO®-1595) at 10 ng/mL into the culture media containing the disc cells significantly suppressed the inflammatory cytokine TNF-α.
Figure 6:
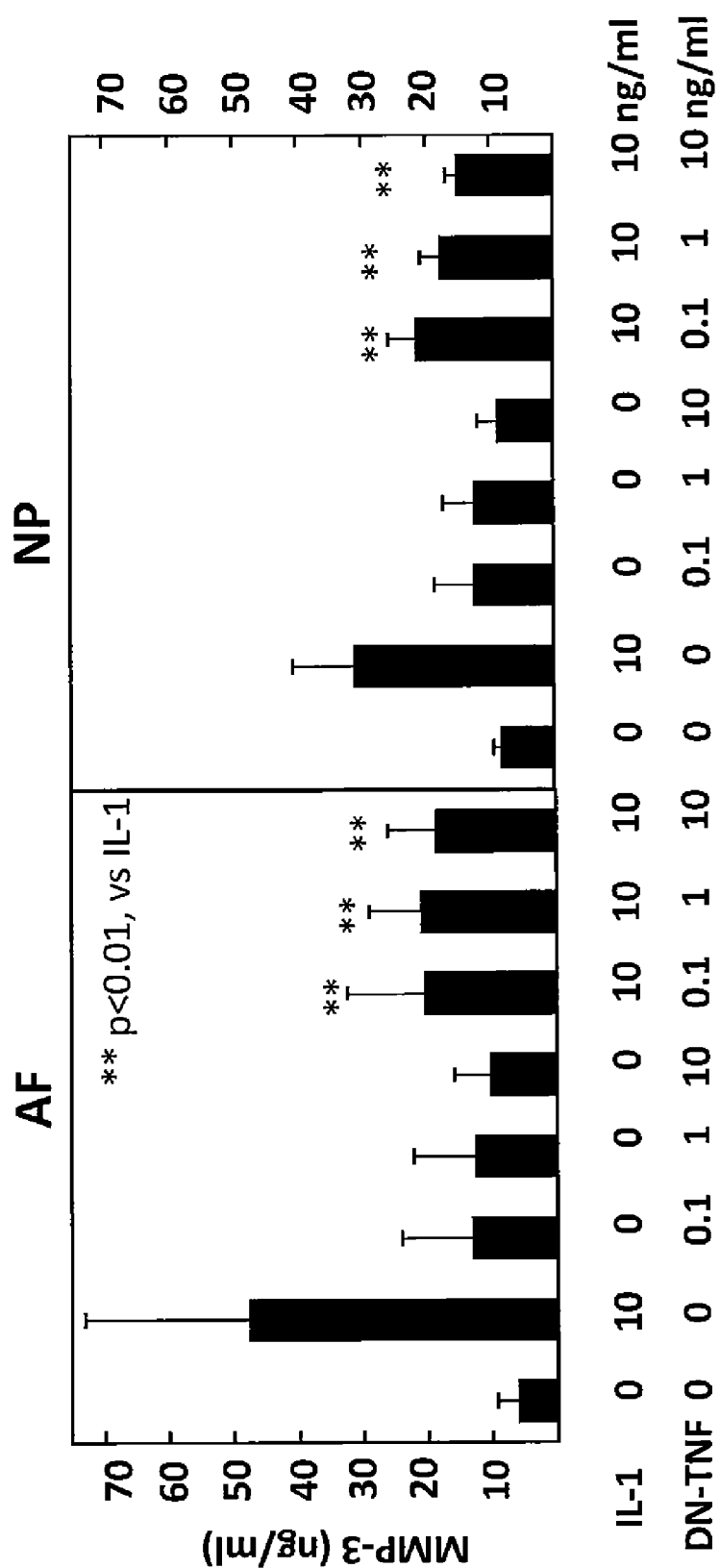
FIG. 6 is a bar graph illustration showing that IL-1β significantly stimulated the release of MMP-3 (matrix metalloproteinase-3) in human intervertebral disc cells and that the addition of DN-TNF (e.g., XPro®-1595) at 10 ng/mL into the culture media containing the disc cells significantly suppressed the inflammatory marker MMP-3.

Effect of DN-TNF on the catabolic activity of human IVD cells: IL-1β significantly stimulated the release of nitrites (% of control: AF 637%; NP 380%; FIG. 4), TNF-α (% of control: AF 217%; NP 223%; FIG. 5) and MMP-3 (% of control: AF 827%; NP 398%; FIG. 6) into media (all p<0.001). These increases were significantly suppressed by the addition of DN-TNF at 10 ng/mL into the culture media (nitrites; % AF 38%, NP 30% [FIG. 4]; TNF-α; % AF 64%, NP 62% [FIG. 5] and MMP-3; % AF 54%, NP 49% [FIG. 6]), p<0.001).

Conclusions

In vitro results show that DN-TNF significantly suppressed the IL-1β-induced release of nitrites, TNF-α and MMP-3 into the media by human IVD cells. This suggests the important involvement of solTNF in IL-1β-induced catabolic events in IVD tissues and provides support for an additional mode of action, in addition to the pain-related effect that other studies using a TNF antibody have suggested. Therefore, the in vivo use of DN-TNF may potentially provide a functional benefit to IVD homeostasis. Additional testing should be performed to determine whether treatment with this novel drug could delay the progression of disc degeneration and/or suppresses pain generation by blocking TNF pathways.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating an intervertebral disc disorder by inhibiting a proinflammatory agent in a patient in need of such treatment, the method comprising administering 0.25 mg/kg to 20 mg/kg of a dominant negative tumor necrosis factor (DN-TNF) antagonist XPRO®-1595 to a target tissue site at or near the intervertebral disc to reduce pain, inflammation, and/or tissue destruction, wherein the proinflammatory agent comprises MMP-3, nitrous oxide, IL-1 or combinations thereof and the DN-TNF is administered in a drug depot comprising polymers comprising poly (lactide-co-glycolide) (PLGA) and polyethylene glycol (PEG) having a molar ratio of 4:1 and a pore forming agent, and the intervertebral disc disorder comprises disc compression, herniated disc, bulging disc, collapsed disc, degenerative disc, back pain, inflamed nerve or combinations thereof, and the DN-TNF antagonist is administered by a continuous infusion over 24 to 48 hours or the DN-TNF antagonist is released over at least 3 days to 6 months.

2. A method according to claim 1, wherein the DN-TNF antagonist is administered before, after or with etanercept, adalimumab, anakinra, infliximab or a combination thereof.

3. A method according to claim 1, wherein the DN-TNF is administered at or in the facet joint, annulus fibrosus, or the nucleus pulposus of the intervertebral disc.

* * * * *